(12) United States Patent
Damadian

(10) Patent No.: US 7,378,846 B1
(45) Date of Patent: May 27, 2008

(54) MAGNETIC RESONANCE IMAGING METHOD AND APPARATUS FOR SCANNING A CHILD

(75) Inventor: Raymond V. Damadian, Woodbury, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 11/170,428

(22) Filed: Jun. 29, 2005

Related U.S. Application Data

(60) Provisional application No. 60/583,859, filed on Jun. 29, 2004.

(51) Int. Cl.
*G01V 3/00* (2006.01)

(52) U.S. Cl. ...................................................... 324/307

(58) Field of Classification Search ........ 324/300–322; 600/410–435
See application file for complete search history.

(56) References Cited

U.S. PATENT DOCUMENTS

| | | | |
|---|---|---|---|
| 4,985,678 A | | 1/1991 | Gangarosa et al. |
| 5,008,624 A | | 4/1991 | Yoshida |
| 5,076,275 A | * | 12/1991 | Bechor et al. ............... 600/410 |
| 5,153,546 A | | 10/1992 | Laskaris |
| 5,339,813 A | * | 8/1994 | DeYoe et al. ............... 600/418 |
| 5,412,419 A | * | 5/1995 | Ziarati ........................... 348/61 |
| 5,436,607 A | | 7/1995 | Chari et al. |
| 5,490,508 A | * | 2/1996 | Kato ........................... 600/422 |
| 5,490,513 A | * | 2/1996 | Damadian et al. ........... 600/415 |
| 5,779,637 A | | 7/1998 | Palkovich et al. |
| 5,825,563 A | * | 10/1998 | Anand .......................... 359/872 |
| 5,861,865 A | * | 1/1999 | Anand et al. ................ 345/658 |
| 5,892,359 A | * | 4/1999 | Yui et al. ..................... 324/318 |
| 6,011,396 A | | 1/2000 | Eckels et al. |
| 6,029,082 A | * | 2/2000 | Srinivasan et al. .......... 600/422 |
| 6,301,497 B1 | * | 10/2001 | Neustadter ................... 600/410 |
| 6,335,623 B1 | * | 1/2002 | Damadian et al. ........... 324/320 |
| 6,434,260 B1 | * | 8/2002 | Soferman et al. ............ 382/131 |
| 6,575,907 B1 | * | 6/2003 | Soferman et al. ............ 600/438 |
| 6,591,128 B1 | * | 7/2003 | Wu et al. ..................... 600/422 |
| 6,611,702 B2 | * | 8/2003 | Rohling et al. .............. 600/415 |
| 7,123,766 B2 | * | 10/2006 | Mao et al. .................... 382/154 |
| 7,127,101 B2 | * | 10/2006 | Littlefield et al. ........... 382/154 |
| 2002/0123681 A1 | | 9/2002 | Zuk et al. |
| 2003/0073910 A1 | * | 4/2003 | Chance ........................ 600/473 |

* cited by examiner

*Primary Examiner*—Brij Shrivastav
*Assistant Examiner*—Dixomara Vargas
(74) *Attorney, Agent, or Firm*—Lerner, David, Littenberg, Krumholz & Mentlik, LLP

(57) ABSTRACT

In one aspect the present invention is a method for imaging an infant or minor in a magnetic resonance imaging apparatus. The method preferably comprises positioning an adult in the patient-receiving space or gap of a magnet and affixing a minor, child or infant with an appropriate antenna. The minor, child or infant is then placed in the lap or arms of the adult and imaging proceeds. In another aspect the method may also comprise positioning an adult and a minor, child or infant in the patient-receiving space or gap of a magnet. The infant, child or minor is placed in closed proximity to the adult so that the infant, child or minor and adult can be fitted with a single antenna. Thereafter, an image of a portion of the minor's, infant's or child's anatomy is obtained.

23 Claims, 2 Drawing Sheets

MAGNETIC RESONANCE IMAGING METHOD AND APPARATUS FOR SCANNING A CHILD

CROSS-REFERENCE TO RELATED APPLICATIONS

This application claims the benefit of the filing date of U.S. Provisional Patent Application No. 60/583,859 filed Jun. 29, 2004, the disclosure of which is hereby incorporated herein by reference.

BACKGROUND OF THE INVENTION

The present invention relates to magnetic resonance imaging systems, apparatus and procedures and, in particular, to apparatus and procedures for safely performing magnetic resonance imaging.

In magnetic resonance imaging, an object to be imaged as, for example, a body of a human subject, is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the precessing automatic nuclei to rotate or "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Many conventional magnetic resonance imaging instruments require that a patient lie on a horizontal bed that is then advanced into a tubular bore within a super-conducting solenoidal magnet used to generate the static magnetic field. Other conventional MRI imaging instruments use a magnet having a ferromagnetic frame defining a patient-receiving space. Considerable effort has been devoted to design of such magnets in a manner which provides a relatively open patient-receiving space, as opposed to the claustrophobic tubular bore of the conventional solenoidal magnet. However, in these instruments as well, it has been the common practice to provide the patient on a bed which remains horizontal throughout the procedure.

Advancement in magnetic resonance imaging has resulted in imaging apparatus that supports a patient in any position between a vertical position and a horizontal position. As described in greater detail in commonly assigned U.S. Pat. No. 6,414,490, which is a continuation of U.S. patent application Ser. No. 08/978,048, and U.S. Pat. No. 6,677,753, the disclosures of which are incorporated by reference herein, a magnetic resonance imaging system can be provided with a patient support, such as a table, which can extend in a generally vertical direction so that the long axis of the patient is substantially vertical. For example, the patient may be in a standing posture, with his back, side or front leaning against a generally vertical patient support. Such a support may include a footrest projecting from the table at its lower end and the patient may stand on the footrest. In other arrangements, the support includes a seat projecting from the table so that the seat is in a horizontal plane when the table surface is vertical. In particularly preferred arrangements, the patient support can move relative to the magnet. For example, the patient support may be arranged to move vertically relative to the magnet so as to elevate a portion of the patient into the imaging volume of the magnet. Alternatively or additionally, the patient support may be arranged to tilt through a range of orientations between a generally horizontal orientation and a generally vertical orientation.

The position of a patient during magnetic resonance imaging may affect or limit the imaging information obtained. A patient may exhibit a symptom if oriented in an upright or weight bearing position and no symptom if oriented in a recumbent or horizontal position. For example, it may be necessary to image a patient in an upright or gravity bearing position to discern a symptom and provide a diagnosis relating to the neck, spine, hip, knee, foot or ankle areas of the human anatomy.

In addition to a patient's position, movement by a patient during imaging may also affect the images obtained. In fact, magnetic resonance imaging procedures generally require the patient to remain perfectly still during imaging. A patient positioned in a weight-bearing upright posture may find it more difficult to remain still during imaging. The anxiety level of a patient is another factor that may affect how still a patient remains during imaging. In general, those magnets that place the patient in the bore of the magnet during imaging tend to add to the patient's anxiety level because of the closed-in and tight environs. A more relaxed patient tends to move less during imaging.

Where an infant or minor is to be scanned, the problem of patient movement takes on additional concern. In particular, that portion of an infant's or minor's anatomical area of interest that is the object of a scan is usually smaller than the same anatomical area in an adult. Thus, any movement by the infant or minor tends to affect the imaging process even more. In addition, a claustrophobic environment tends to cause even more unwanted movement on the part of the child or infant. Indeed, children under 12 are almost always anesthetized, requiring continuous cardiac and respiratory monitoring and an attending anesthesiologist. As such, children are asked to endure a certain level of discomfort and are exposed to considerable risk caused by the application of anesthesia. In addition, parents are caused undue anxiety and the hospital incurs extra costs and is exposed to unnecessary risk associated with the application of anesthesia.

In the case where the subject is a premature infant, imaging the premature infant outside an incubator poses very serious health risks. Indeed, in most cases imaging a premature infant in an MRI scanner is not an option as the infant needs to remain in the incubator.

Of utility then are methods, apparatus, and systems that enable magnet resonance imaging of infants, premature or otherwise, and children.

SUMMARY

In one aspect, the present invention provides a method for magnetic resonance imaging. The method preferably comprises positioning a first person in a patient-receiving space of a magnet resonance imaging apparatus. A child is then positioned in the patient-receiving space of the magnetic resonance imaging apparatus in close proximity to the adult. A magnetic resonance image of a portion of the child's anatomy is thereafter acquired.

The method may further desirably comprise affixing an antenna coil to the child.

Further in accordance with this aspect of the present invention, positioning the child comprises placing the child on the first person's lap in a sitting position. Positioning may also further desirably include placing the child on the first person's lap in a recumbent position or in an upright position.

Further in accordance with this aspect of the present invention, positioning the first person comprises positioning the first person in an upright position in the patient-receiving space. It may also prove desirable to have the first person oriented in a sitting position in the patient-receiving space. In addition, it may also prove advantageous to be able to have the first person standing while holding the child.

Further in accordance with this aspect of the present invention, positioning the first person may comprise placing the first person in the receiving space of a magnetic resonance imaging apparatus comprising first and second elements disposed along a horizontal axis and defining a patient-receiving space therebetween capable of accepting a patient in a weight-bearing position.

Further still, the child may be an infant or a minor under 12 years old. Most preferably, the first person is an adult that assists in comforting the child.

In another aspect, the present invention is a method for magnetic resonance imaging comprising positioning an adult in a patient-receiving space of a magnetic resonance imaging apparatus and positioning s child in the patient-receiving space of the magnetic resonance imaging apparatus in close proximity to the adult. The method further desirably comprises placing an antenna coil around the adult and the child and acquiring a magnetic resonance image of a portion of the infant's anatomy.

Further in accordance with this aspect of the present invention, the method further comprises positioning a display device within a field of view of the child positioned in the receiving space of the magnetic resonance imaging apparatus.

In another aspect the present invention is a method for performing magnetic resonance imaging. The method preferably comprises positioning a child in a patient-receiving space of a magnet resonance imaging magnet so that the child can directly view a display device, and obtaining magnet resonance images of the child's anatomy.

Further in accordance with this aspect of the present invention, positioning the child further preferably comprises fitting the child with a receiving coil.

In addition, the method may further comprise displaying an image or video program on the display device.

Other advantages and details of the present invention will be explained by reference to the following drawings and detailed description.

DETAILED DESCRIPTION

Figure 1:
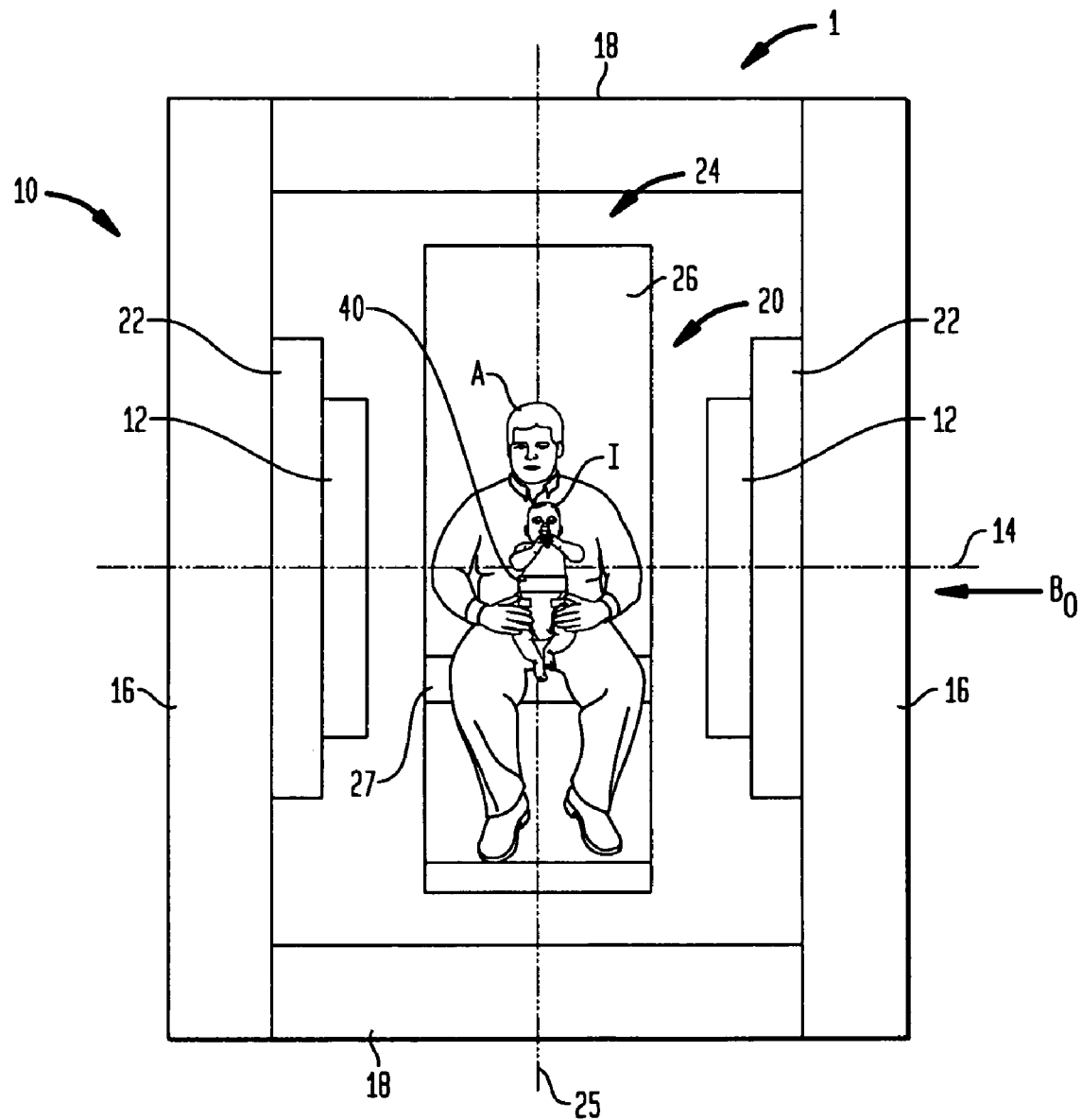
FIG. 1 depicts an infant and a first person positioned in the patient-receiving space of a magnetic resonance imaging apparatus in accordance with an aspect of the present invention.

FIG. 1 illustrates a front view of an apparatus 1 in accordance with an aspect of the present invention. The apparatus 1 includes a static field magnet having a frame 10 including a pair of poles 12 spaced apart from one another along a horizontal pole axis 14. Frame 10 further includes flux conducting and return members that, in the particular embodiment illustrated, include a pair of sidewalls 16 and columns 18 extending between the sidewalls 16. The particular frame depicted in FIG. 1 is generally in accordance with the aforementioned U.S. Pat. No. 6,677,753 (hereinafter "the '753 patent"), the disclosure of which is incorporated by reference herein in its entirety, although other configurations can be employed. The apparatus 1 is manufactured and marketed under the trademark STAND-UP MRI by Fonar Corp. of New York, the assignee of the present invention. The opposed poles define a patient-receiving space or gap 20 between them. The magnet further includes a source of magnetic flux adapted to direct into and out of the gap through poles 12 so as to form a static magnetic field having a field vector $B_0$ in the horizontal direction, parallel to pole axis 14. In the particular embodiment illustrated, the flux source includes a pair of electromagnet coils 22 encircling poles 12. These coils may be superconductive or resistive coils. Alternate flux sources such as coils disposed at other locations along the ferromagnetic frame and permanent magnets also may be employed.

Figure 2:
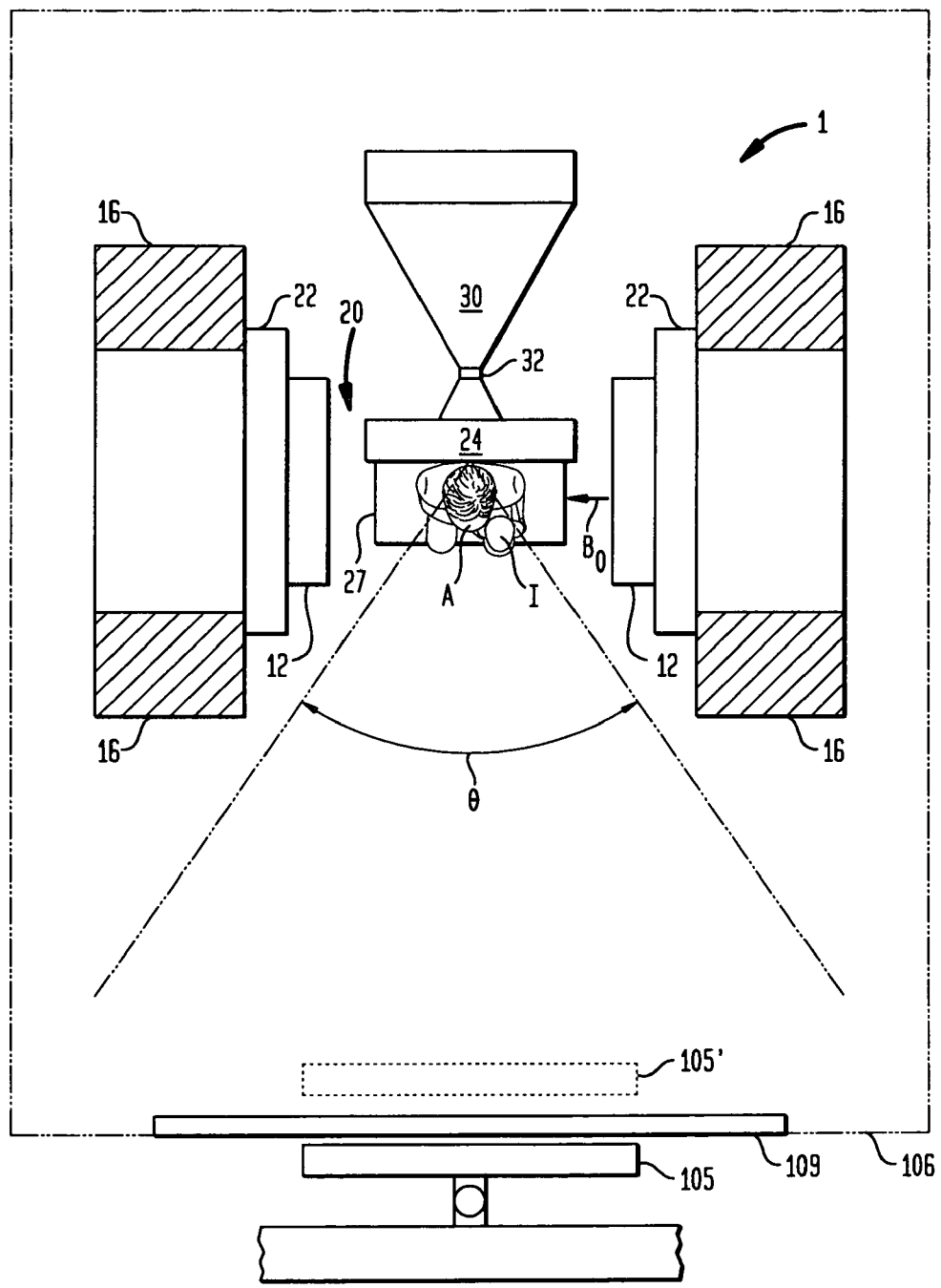
FIG. 2 is a top view of an infant and a first person positioned in the patient-receiving space of a magnetic resonance imaging system in accordance with an additional aspect of the present invention.

The apparatus 1 further includes a patient support assembly including a bed 24 defining an elongated patient supporting surface 26 having a lengthwise axis 25 and a platform 28 projecting from the supporting surface at a foot end of the bed. In addition, a seat 27 may be mounted to supporting surface 26 to allow a patient to be positioned in a sitting position. As best seen in FIG. 2, the patient supporting assembly further includes a frame 30. Bed 24 is pivotally mounted to the frame 30 for movement about a generally horizontal pivot axis 32. Pivot axis 32 is substantially parallel to pole axis 14. Bed 24 can pivot between an upright position in which the lengthwise direction over the bed extends generally vertically as seen in FIG. 1 and a fully horizontal position, in which the lengthwise direction of the bed 24 extends horizontally. As further described in the '753 patent, bed 24 also may be mounted for vertical motion relative to a frame and hence relative to the static field magnet 10. Moreover, a frame can be mounted for horizontal movement relative to the static field magnet. Appropriate actuators and control devices are provided for moving the bed and for moving the support frame.

Although FIGS. 1 and 2 illustrate a particular magnet configuration, other configurations may be employed in accordance with the present invention. In general, any magnetic resonance imaging apparatus that is able to accommodate an adult and infant simultaneously within the patient-receiving gap or space will be used in accordance with this aspect of the present invention. For example, the magnet configurations disclosed in commonly assigned U.S. patent application Ser. No. 10/725,155, also filed on Dec. 1, 2003, the disclosure of which is incorporated by reference herein, may also be used in accordance with the present invention.

As is also shown in FIG. 1, an infant I is equipped with an antenna coil 40, which enables reception of magnetic resonance signals that may be emitted by the portion of the infant's anatomy which is of interest. Alternatively, other antenna arrangements such as transmitting and receiving antennas arranged within the magnet structure may be used to transmit and receive radio frequency signals to the infant I in lieu of affixing the antenna coil 40 to the infant I. The infant I is shown as being seated in the lap of a person, preferably, an adult A. Although the infant I is shown as being seated, the infant may be positioned in any other position that assists in reducing movement during imaging. Specifically, the infant may lie or stand on the adult's lap or may be placed on the adult's shoulder. In accordance with this aspect of the present invention, by having the infant and the adult in the patient-receiving space at the same time, the adult is able to comfort the infant resulting in less unwanted movement. As such, imaging may be done more quickly. In accordance with this aspect of the present invention, an infant may comprise an infant, minor or child of any age between recently born to youth who is comforted by an adult during the imaging process. In addition, in cases of mental retardation, etc., the actual age of the person who will be imaged may vary well beyond the age of a normal youth.

Although it is preferable that the person, denoted as A, in the patient-receiving space be an adult and most preferably the infant's parent, anyone who is able to enhance the comfort level of the infant or minor may be used to hold the infant I. As such, the adult A may comprise a doctor, nurse, or any other person available to assist in the procedure.

In addition, in an alternative embodiment instead of fitting the child with an antenna coil, such as coil 40, it may prove advantageous to wrap an adult size antenna coil around both the adult A and infant I and perform imaging of the infant's I anatomy. Further in this regard, it may also prove advantageous to tether the antenna 40 to a belt or other strap that is fitted to the adult. In this latter variant, tethering the infant's antenna coil 40 to the adult further assists in reducing movement during imaging.

Furthermore, although in the foregoing description an infant was the object of imaging (i.e., the patient), the infant may be replaced by a child of any age that does not feel comfortable being imaged alone. In that regard, this aspect of the present invention is not dependent on the age of the child or infant. Rather, as long as another person can fit within the patient receiving space with the child or patient so that more costly and risk procedures, e.g., sedating the patient, may be avoided, the benefits of this aspect of the present invention can be achieved.

FIG. 2 illustrates a top view of an infant and adult positioned in the patient-receiving space of a magnetic resonance imaging system in accordance with an additional aspect of the present invention. As shown, the system includes a magnetic resonance imaging apparatus 1 in combination with a display device 105 that is placed within a viewing angle, θ, of the patient. The display device 105 may be a cathode ray tube (CRT) type monitor, a plasma type display, including a flat screen plasma monitor, a rear projection screen or any other device that allows viewing of moving or still images. The apparatus 1, because of its open design, does not obstruct the patient's field of view, thereby allowing a patient a view of the area outside the magnet, i.e., the scanner room, from inside the magnet. Thus, infant I (or a child) and adult A may view the display device 105 while the infant's anatomy is imaged or scanned. During the imaging process the display device 105 is preferably equipped to display programming of the infant's choice or programming selected by an adult, such as the infant's parent, to appear on the display device. We have found that allowing an infant I (or a child) to view a movie or other programming during the imaging process further reduces any unwanted movement on the part of the infant or child. Thus, the imaging process proceeds more efficiently by reducing the number of times a particular scan has to be repeated. As such, images of the infant's anatomy may be obtained more quickly.

In accordance with a preferred embodiment, the display device 105 is placed outside the shielded room 106 and viewable through a shielding 109. In an embodiment the shielding 109 comprises an electrically conductive wire screen that may be preferably made using copper. Alternatively, the display device 105 may be placed behind magnetically and/or electro-magnetically shielded glass.

In a further variant, a display device 105' may be placed inside the room 106, provided the display device 105' does not affect the normal functioning of the magnetic resonance imaging system. For example, detection of the magnetic resonance imaging signals that are emitted by a patient's anatomy may be compromised by any electromagnetic interference generated by a display device. Conversely, the magnetic or electromagnetic characteristics of the imaging system may affect the operation of the display device 105' or other ancillary equipment needed to provide programming. In accordance with this variant, a non-metallic projection screen may be placed in the shield room 106 within the infant's or adult's viewing angle θ. A rear projecting apparatus may then project a program, including moving or still images, onto the projection screen. Other details associated with providing a display device in combination with a magnetic resonance imaging apparatus are included in commonly assigned U.S. patent application Ser. No. 10/816,526, filed on Apr. 1, 2004, entitled "INCREASING THROUGHPUT IN MAGNETIC RESONANCE IMAGING," the disclosure of which is incorporated by reference herein in its entirety.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for magnetic resonance imaging, comprising:
   positioning a first person in a patient-receiving space of a magnetic resonance imaging apparatus;
   positioning a child in the patient-receiving space of the magnetic resonance imaging apparatus so that the child is supported by an exterior portion of the first person's anatomy; and acquiring a magnetic resonance image of a portion of the child's anatomy, wherein any data acquired from the first person is discernible from the child's image.

2. The method of claim 1, further comprising affixing an antenna coil to the child.

3. The method of claim 1, wherein positioning the child comprises placing the child on the first person's lap in a sitting position.

4. The method of claim 1, wherein positioning the child comprises placing the child on the first person's lap in a recumbent position.

5. The method of claim 1, wherein positioning the child comprises placing the child on the first person's lap in an upright position.

6. The method of claim 1, wherein positioning the first person comprises positioning the first person in an upright position in the patient-receiving space.

7. The method of claim 6, wherein positioning the first person further comprises orienting the first person in a sitting position in the patient-receiving space.

8. The method of claim 6, wherein positioning the first person further comprises orienting the first person in a standing position in the patient-receiving space.

9. The method of claim 1, wherein positioning the first person comprises placing the first person in the receiving space of a magnetic resonance imaging apparatus comprising first and second poles disposed along a horizontal axis and defining a patient-receiving space therebetween capable of accepting a patient in a weight-bearing position.

10. The method of claim 1 further comprising positioning a display device within a field of view of the child positioned in the receiving space of the magnetic resonance imaging apparatus.

11. The method of claim 1, wherein the child is an infant.

12. The method of claim 1, wherein the first person is an adult.

13. A method for performing magnetic resonance imaging according to claim 1, further comprising:

positioning a child in a patient-receiving space of a magnet resonance imaging magnet so that the child can directly view a display device, and obtaining magnet resonance images of the child's anatomy.

14. The method of claim 13, wherein positioning the child further comprises fitting the child with a receiving coil.

15. The method of claim 14, further comprising displaying an image on the display device.

16. The method of claim 14, further comprising displaying a video program on the display device.

17. A method for performing magnetic resonance imaging of a child, comprising:

positioning an adult in a patient-receiving space of a magnetic resonance imaging apparatus;

positioning a child in the patient-receiving space of the magnetic resonance imaging apparatus so that the child is supported by an exterior portion of the adult's anatomy;

placing an antenna coil around the adult and the child; and acquiring a magnetic resonance image of a portion of the child's anatomy, wherein any data acquired from the parent's anatomy is discernible from the child's image.

18. The method of claim 17, wherein positioning the child comprises placing the child on the adult's lap in a sitting position.

19. The method of claim 17, wherein positioning the child comprises placing the child on the adult's lap in an upright position.

20. The method of claim 17, wherein positioning the adult further comprises orienting the adult in a standing position in the patient-receiving space.

21. The method of claim 17 further comprising positioning a display device within a field of view of the child positioned in the receiving space of the magnetic resonance imaging apparatus.

22. The method of claim 17, wherein the child is an infant.

23. The method of claim 22, wherein the child is a minor less than 12 years old.

* * * * *